US008017154B2

(12) United States Patent
Akashi et al.

(10) Patent No.: US 8,017,154 B2
(45) Date of Patent: Sep. 13, 2011

(54) POLYAMINO ACID FOR USE AS ADJUVANT

(75) Inventors: Mitsuru Akashi, Osaka (JP); Masanori Baba, Kagoshima (JP)

(73) Assignees: Mitsuru Akashi, Osaka (JP); Masanori Baba, Kagoshima (JP)

( * ) Notice: Subject to any disclaimer, the term of this patent is extended or adjusted under 35 U.S.C. 154(b) by 9 days.

(21) Appl. No.: 12/458,895

(22) Filed: Jul. 27, 2009

(65) Prior Publication Data

US 2009/0285901 A1 Nov. 19, 2009

Related U.S. Application Data

(62) Division of application No. 11/918,892, filed as application No. PCT/JP2006/308218 on Apr. 19, 2006, now Pat. No. 7,785,612.

(30) Foreign Application Priority Data

| Apr. 20, 2005 | (JP) | 2005-122650 |
|---|---|---|
| Aug. 2, 2005 | (JP) | 2005-224519 |
| Sep. 16, 2005 | (JP) | 2005-270146 |

(51) Int. Cl.
| A61K 9/14 | (2006.01) |
|---|---|
| A61K 9/51 | (2006.01) |
| A61K 39/385 | (2006.01) |
| A61K 39/12 | (2006.01) |
| A61K 39/145 | (2006.01) |
| A61K 39/21 | (2006.01) |
| A61K 39/215 | (2006.01) |
| C12N 7/00 | (2006.01) |

(52) U.S. Cl. ............ 424/489; 424/499; 424/196.11; 424/204.1; 424/207.1; 424/208.1; 424/209.1; 424/218.1; 424/221.1; 435/235.1

(58) Field of Classification Search ................. None
See application file for complete search history.

(56) References Cited

U.S. PATENT DOCUMENTS

| 5,700,459 | A | 12/1997 | Krone et al. | |
|---|---|---|---|---|
| 7,105,162 | B1 | 9/2006 | Schmidt et al. | |
| 2004/0022840 | A1* | 2/2004 | Nagy et al. | 424/450 |
| 2004/0057958 | A1 | 3/2004 | Waggoner, Jr. et al. | |
| 2008/0152615 | A1 | 6/2008 | Sung et al. | |

FOREIGN PATENT DOCUMENTS

| JP | 4-225915 | | 8/1992 |
|---|---|---|---|
| JP | 11-504655 | | 4/1999 |
| JP | 2000-506125 | | 5/2000 |
| JP | 2005-187427 | | 7/2005 |
| WO | 97/02022 | | 1/1997 |
| WO | WO 00/12124 | * | 3/2000 |
| WO | 2005/000884 | | 1/2005 |
| WO | 2006/090968 | | 8/2006 |

OTHER PUBLICATIONS

Benson et al (AIDS Research and Human Retroviruses 15:105-113, 1999).*
Matsusaki et al (Chemistry Letters 33:398-399, 2004).*
Akagi et al (Journal of Medical Virology 69:163-172, 2003).*
Walker et al. Science May 9, 2008 320: 760-764.*
Gallo, R. C. The Lancet, vol. 366, Issue 9500, Nov. 26, 2005-Dec. 2, 2005, pp. 1894-1898.*
Staprans et al. Expert Review of Vaccines, vol. 3, No. 4s1, pp. S5-S32., Aug. 2004.*
European Patent Office Office Action dated Mar. 1, 2010 issued in corresponding European Patent Application No. 06 745 450.4, in the English language.
International Search Report issued Jul. 25, 2006 in the International (PCT) Application PCT/JP2006/308218 of which the parent application is the U.S. National Stage.
Mitsuru Akashi, "Development of antiretroviral vaccine applying nanoparticle", Heisei 14 Nendo Basic Research Programs Kenkyu Nenpo, pp. 1-2, 2004 with partial English translation.
Michiya Matsusaki et al., "Stably-dispersed and Surface-functional Bionanoparticles Prepared by Self-assembling Amphipathic Polymers of Hydrophilic Poly(γ-glutamic acid) Bearing Hydrophobic Amino Acids", Chemistry Letters, vol. 33, No. 4, pp. 398-399, 2004.
Tatsuo Kaneko et al., "Self-assembled Soft Nanofibrils of Amphipathic Polypeptides and Their Morphological Transformation", Chem. Mater., vol. 17, pp. 2484-2486, 2005.
Takami Akagi et al., "In vitro Enzymatic Degradation of Nanoparticles Prepared from Hydrophobically-Modified Poly (γ-glutamic acid)", Macromol. Biosci., vol. 5, pp. 598-602, 2005.
Takami Akagi et al., "Preparation and characterization of biodegradable nanoparticles based on poly (γ-glutamic acid) with L-phenylalanine as a protein carrier", Journal of Controlled Release, vol. 108, pp. 226-236, 2005.
Tamaki Akagi et al., "Hydrolytic and Enzymatic Degradation of Nanoparticles Based on Amphiphilic Poly(γ-glutamic acid)-graft-L-Phenylalanine Copolymers", Biomacromolecules, vol. 7, pp. 297-303, 2006.
Tamaki Akagi et al., "Multifunctional conjugation of proteins on/into bio-nanoparticles prepared by amphiphilic poly(γ-glutamic acid)", J. Biomater. Sci. Polymer Edn., vol. 17, No. 8, pp. 875-892, 2006.
Tamaki Akagi et al., "Protein direct delivery to dendritic cells using nanoparticles based on amphiphilic poly (amino acid) derivatives", Biomaterials, vol. 28, pp. 3427-3436, 2007.
Keisuke Matsuo et al., "Efficient generation of antigen-specific cellular immunity by vaccination with poly (γ-glutamic acid) nanoparticles entrapping endoplasmic reticulum-targeted peptides", Biochemical and Biophysical Research Communications, vol. 362, pp. 1069-1072, 2007.
Tamaki Akagi et al., "Preparation of nanoparticles by the self-organization of polymers consisting of hydrophobic and hydrophilic segments: Potential applications", Polymer, vol. 48, pp. 6729-6747, 2007.

(Continued)

Primary Examiner — Mary E Mosher
(74) Attorney, Agent, or Firm — Wenderoth Lind & Ponack, L.L.P.

(57) ABSTRACT

Use of a polyamino acid as an adjuvant; an application of a polyamino acid as an adjuvant in the production of a vaccine; a vaccine comprising a polyamino acid as an adjuvant; a biodegradable nanoparticle having a virus antigen immobilized thereon; and a vaccine comprising the biodegradable nanoparticle.

12 Claims, 7 Drawing Sheets

OTHER PUBLICATIONS

English translation of International Preliminary Report on Patentability dated Mar. 13, 2008 in the International (PCT) Application PCT/JP2006/308218 of which the parent application is the U.S. National Stage.

Xin Wang et al., "Poly(-Glutamic Acid) Nanoparticles as an Efficient Antigen Delivery and Adjuvant System: Potential for an AIDS Vaccine", Journal of Medical Virology, vol. 80, pp. 11-19, 2008.

Akashi, M., "Development of Anti-retroviral Vaccine Using Nanoparticles", 15 Nendo Nenpo, pp. 110-113, 2004 (with full English translation).

Supplementary European Search Report dated Dec. 15, 2008 in European Application No. 06 74 5450 corresponding to the parent application.

M. Akashi et al., "Protein Direct Delivery to Dendritic Cells Using Polymeric Nanospheres Consisting of Poly(gamma-Glutamic Acid) Derivatives for Vaccination", Polymer Preprints, vol. 47, No. 2, pp. 134-135, XP003022149, Jan. 1, 2006.
Taia T. Wang et al. "Induction of Opsonic Antibodies to the gamma-D-Glutamic Acid Capsule of *Bacillus anthracis* by Immunization with a Synthetic Peptide-Carrier Protein Conjugate", FEMS Immunology and Medical Microbiology, Elsevier Science, vol. 40, No. 3, pp. 231-237, XP002306077, ISSN: 0928-8244, Apr. 9, 2004.
Lechner et al., Intervirology 45(4-6): 212-217, 2002.
Benson et al., AIDS Research and Human Retroviruses 15 (2): 105-113, 1999.
Office Action dated Sep. 22, 2009 in U.S. Appl. No. 11/918,892, which is the parent to the present U.S. application.
Office Action issued Mar. 1, 2010 in parent application U.S. Appl. No. 11/918,892 of present divisional application.
European Search Report dated Aug. 24, 2010 issued in corresponding European Patent Application No. 06745450.4.

* cited by examiner

| CELL | CD40 | CD80 | CD86 | MHC CLASS I | MHC CLASS II |
|---|---|---|---|---|---|
| iDC | 100 | 100 | 100 | 100 | 100 |
| mDC | 460 | 226 | 227 | 268 | 275 |
| iDC + γ-PGA NANOPARTICLE (75 μg/ml) | 173 | 97 | 91 | 180 | 140 |
| iDC + γ-PGA NANOPARTICLE (150 μg/ml) | 233 | 83 | 157 | 213 | 160 |
| iDC + γ-PGA NANOPARTICLE (300 μg/ml) | 353 | 86 | 227 | 235 | 148 |

MEASUREMENT IS VALUE DEFINING THE EXPRESSION (AVERAGE FLUORESCENCE INTENSITY) IN iDC AS 100

| CELL | AMOUNT OF $^3$H-THYMIDINE INCORPORATED |
|---|---|
| T CELL ALONE | 9±4 |
| mDC ALONE | 15±6 |
| T CELL + iDC | 100 |
| T CELL + mDC | 338±126 |
| T CELL + iDC DIFFERENTIATED BY 75 μg/ml γ-PGA NANOPARTICLE | 255±13 |
| T CELL + iDC DIFFERENTIATED BY 150 μg/ml γ-PGA NANOPARTICLE | 545±87 |
| T CELL + iDC DIFFERENTIATED BY 300 μg/ml γ-PGA NANOPARTICLE | 1427±440 |

VALUE DEFINING THE AMOUNT OF $^3$H-THYMIDINE INCORPORATION IN THE CASE OF T CELL + iDC AS 100

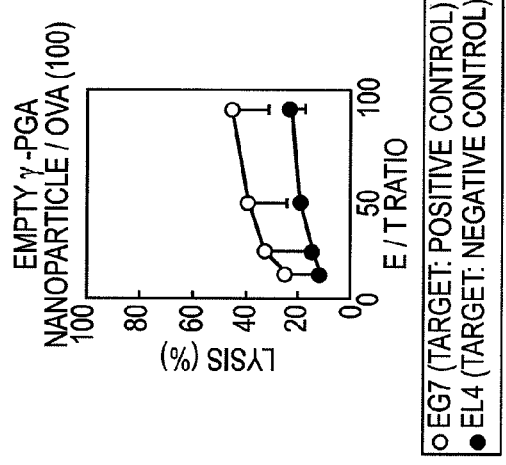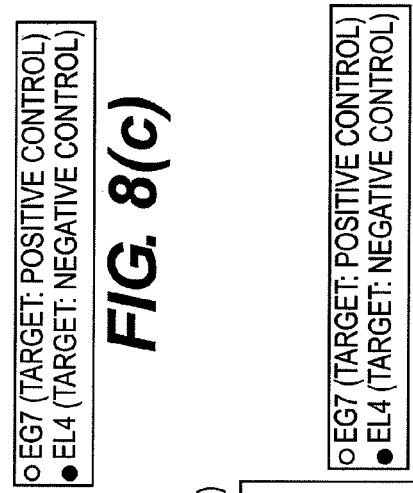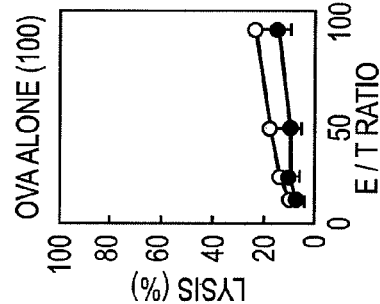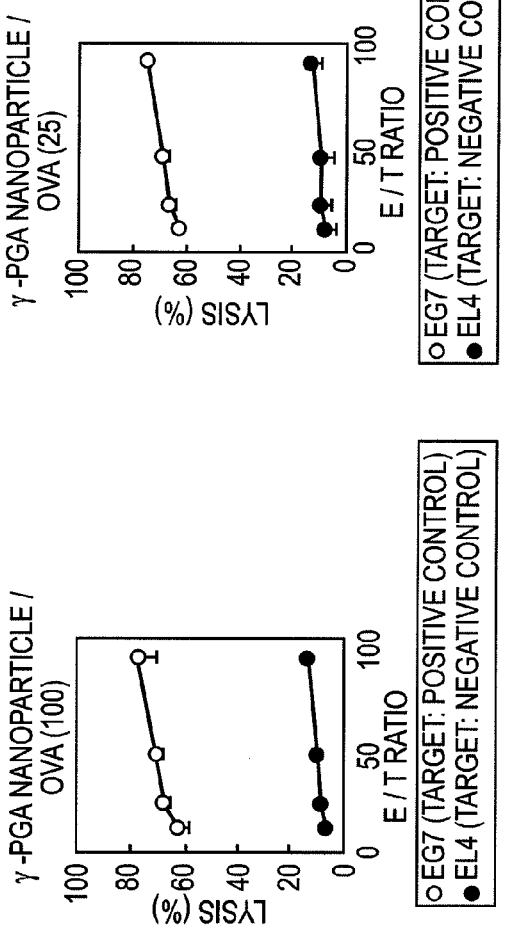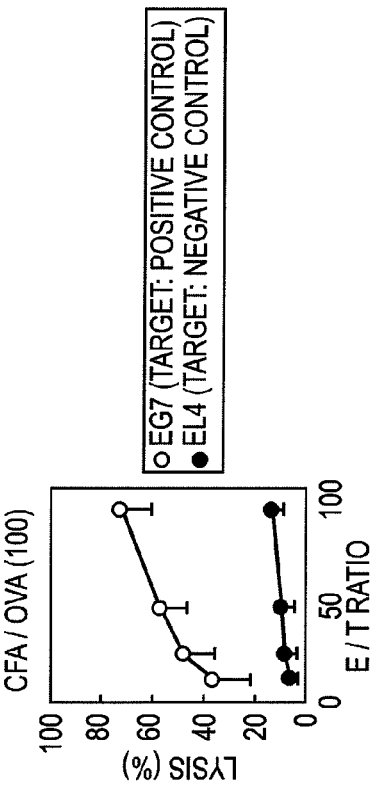

POLYAMINO ACID FOR USE AS ADJUVANT

The present application is a divisional application of Ser. No. 11/918,892, filed Mar. 14, 2008, now U.S. Pat. No. 7,785,612 which is 371 application of PCT/JP2006/308218, filed Apr. 19, 2006.

TECHNICAL FIELD

The present invention relates to use of a polyamino acid as an adjuvant, use of a polyamino acid as an adjuvant for the manufacture of a vaccine, and a vaccine comprising a polyamino acid as an adjuvant. The present invention further relates to a nanoparticle to which an antigen is immobilized and use thereof as a vaccine.

BACKGROUND

Various vaccines have been developed and used to prevent and treat a wide variety of diseases including viral diseases. However, when an antigen such as a viral protein is administered alone into a living body, stability of the antigen molecule in the living body is low, and efficiency of incorporation thereof into cells is insufficient. Then, efforts have been made in current vaccine therapies, for example, by administering a mixture formed by emulsification with an appropriate particulate carrier or immunostimulatory agent (adjuvant). However, for example, there has been no report of a case in which a preexisting adjuvant is successfully used for an HTLV-1 vaccine in an HTLV-1 infection. This is because the activity of cytotoxic T lymphocytes (CTLs) against HTLV-1 and frequency of existence thereof in a living body are low. Furthermore, for example, attempts have been made to treat an infection with a virus such as HIV or a cancer in a patient by inducing CTLs which attack specifically the infected cells or cancer cells. In such treatment, it is considered to be important whether CTLs can be induced effectively. For this purpose, an adjuvant such as Freund's adjuvant or aluminum hydroxide is usually used. However, no satisfactory result in respect of the safety or efficacy has been achieved. Thus, it is has not been reported that a polyamino acid, in particular poly(γ-glutamic acid), exhibits an excellent effect as an adjuvant as described herein.

Recently, researches on and development of nanoparticles have been promoted because the nanoparticles are expected to play novel roles in various fields due to their size. Attempts have also been made to utilize nanoparticles for therapies. For example, a nanoparticle is used as a carrier for a drug in some studies (see Patent Documents 1 and 2). However, there is concern for the influence of the nanoparticle on a living body, because its behavior in the body has not yet been elucidated and, therefore, the toxicity or safety is uncertain. It is essential for the actual contribution to medical service to practically develop a biodegradable nanoparticle that can substitute for the undegradable nanoparticles. There has also been concerned that the activity of an antigen is lost, for example, by denaturation or degradation upon binding of the antigen to a nanoparticle, and the nanoparticle can not exhibit the function as an adjuvant. Thus, there has been no report on use, as an adjuvant, of a polyamino acid, in particular poly(γ-glutamic acid), that is prepared as a nanoparticle, a nanoparticle to which an antigen is immobilized, or use thereof as a vaccine as described herein.

Patent Document 1: JP-A-92870/1994
Patent Document 2: JP-A-256220/1994

DISCLOSURE OF INVENTION

Problems to be Solved by the Invention

The problems to be solved by the present invention are to provide a safe and effective adjuvant for a vaccine, as well as to provide a vaccine utilizing the same.

Means to Solve the Problems

As a result of intensive studies in view of the situation as described above, the present inventors have found that a polyamino acid, in particular, poly(γ-glutamic acid) promotes differentiation and maturation of a dendritic cell, that is, it acts as an adjuvant, moreover the action is increased by preparing as nanoparticles. Thus, the present invention has been completed.

The present invention provides:
(1) use of a polyamino acid as an adjuvant;
(2) the use according to (1), wherein the polyamino acid is selected from the group consisting of poly(γ-glutamic acid), poly(α-aspartic acid), poly(ε-lysine), poly(α-glutamic acid), poly(α-lysine), polyasparagine, modified forms or derivatives thereof, and mixtures thereof;
(3) the use according to (2), wherein the polyamino acid is poly(γ-glutamic acid);
(4) the use according to (1), wherein the polyamino acid is in the amphiphilic form;
(5) the use according to any one of (1)-(4), wherein the polyamino acid is prepared as a nanoparticle;
(6) use of a polyamino acid as an adjuvant for the manufacture of a vaccine;
(7) the use according to (6), wherein the polyamino acid is selected from the group consisting of poly(γ-glutamic acid), poly(α-aspartic acid), poly(ε-lysine), poly(α-glutamic acid), poly(α-lysine), polyasparagine, modified forms or derivatives thereof, and mixtures thereof;
(8) the use according to (7), wherein the polyamino acid is poly(γ-glutamic acid);
(9) the use according to (6), wherein the polyamino acid is in the amphiphilic form;
(10) the use of according to any one of (6)-(9), wherein the polyamino acid is prepared as a nanoparticle;
(11) a vaccine comprising a polyamino acid as an adjuvant;
(12) the vaccine according to (11), wherein the polyamino acid is selected from the group consisting of poly(γ-glutamic acid), poly(α-aspartic acid), poly(ε-lysine), poly(α-glutamic acid), poly(α-lysine), polyasparagine, modified forms or derivatives thereof, and mixtures thereof;
(13) the vaccine according to (12), wherein the polyamino acid is poly(γ-glutamic acid);
(14) the vaccine according to (11), wherein the polyamino acid is in the amphiphilic form;
(15) the vaccine according to any one of (11)-(14), wherein the polyamino acid is prepared as a nanoparticle;
(16) a biodegradable nanoparticle, to which a virus antigen is immobilized;
(17) the biodegradable nanoparticle according to (16), wherein the viral antigen is selected from the group consisting of a retroviral antigen, an influenza viral antigen, a flaviviral antigen, a diarrhea viral antigen and a coronaviral antigen;
(18) the biodegradable nanoparticle according to (17), wherein the viral antigen is a retroviral antigen;
(19) the biodegradable nanoparticle according to (18), wherein the retroviral antigen is an HIV antigen;

(20) the biodegradable nanoparticle according to any one of (16)-(19), which has a polyamino acid as its backbone;

(21) the biodegradable nanoparticle according to (20), wherein the polyamino acid is selected from the group consisting of poly(γ-glutamic acid), poly(α-aspartic acid), poly (ε-lysine), poly(α-glutamic acid), poly(α-lysine), polyasparagine, modified forms or derivatives thereof, and mixtures thereof;

(22) the biodegradable nanoparticle according to (21), wherein the polyamino acid is poly(γ-glutamic acid);

(23) the biodegradable nanoparticle according to (20), wherein the polyamino acid is in the amphiphilic form;

(24) the biodegradable nanoparticle according to any one of (16)-(23), wherein the antigen is incorporated into the nanoparticle;

(25) the biodegradable nanoparticle according to any one of (16)-(23), wherein the antigen is present on the surface of the nanoparticle;

(26) a vaccine comprising the biodegradable nanoparticle according to any one of (16)-(25);

(27) the vaccine according to (26), which is an anti-HIV vaccine;

(28) a method for the immunization of a subject, comprising administering the vaccine according to (26) to the subject;

(29) a method for the treatment and/or prevention of a disease in a subject, comprising administering the vaccine according to (26) to the subject;

(30) the method according to (29), wherein the disease is HIV;

(31) use of the biodegradable nanoparticle according to any one of (16)-(25) for the manufacture of a vaccine for the treatment and/or prevention of a disease;

(32) the use according to (31), wherein the disease is HIV.

Effects of the Invention

The present invention provides use as an adjuvant of a polyamino acid which is highly safe because it is biodegradable, use thereof for the manufacture of a vaccine, as well as a vaccine comprising a polyamino acid as an adjuvant.

BRIEF DESCRIPTION OF DRAWINGS

FIG. 8 represents results of experiments for inducing CTL induction using by OVA-immobilized γ-PGA nanoparticles.

BEST MODE FOR CARRYING OUT THE INVENTION

Figures 1, 2:
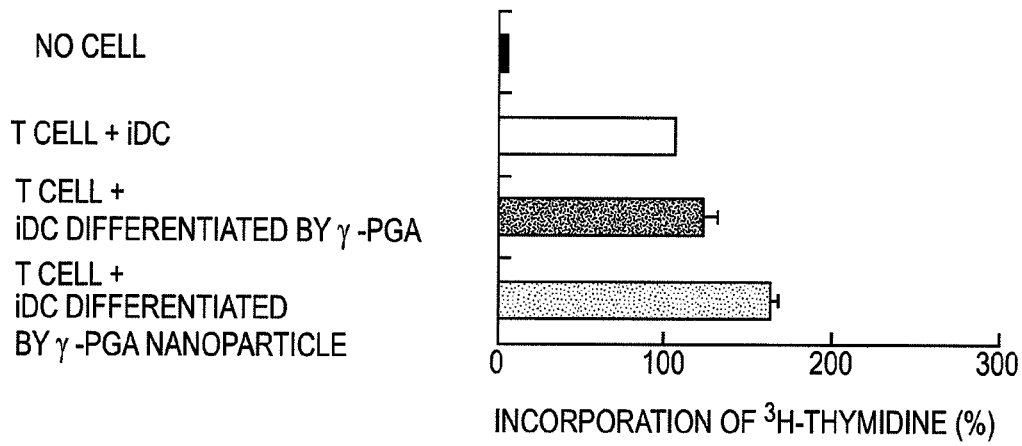
FIG. 1 is a graph which represents changes in amounts of $^3$H-thymidine incorporation into T-lymphocytes resulting from preparation of γ-PGA as nanoparticles.
FIG. 2 represents results of surface molecule expression on dendritic cells, which are measured by a flow cytometer.

In one aspect, the present invention relates to use of the polyamino acid as an adjuvant. The adjuvant means a substance that stimulates an immune system to enhance an immunoreaction. The adjuvant allows, for example, to promote differentiation and maturation of a dendritic cell, to activate a T cell, to promote secretion of various cytokines and to increase a CTL induction rate.

The polyamino acid used in the present invention may be composed of any amino acids. It may comprise a component other than the amino acid, for example, a saccharide or a lipid. It is preferable that the polyamino acid has as its main material or backbone a polypeptide consisting of amino acids, and 50% or more of its component is constituted by the amino acids. The constituting amino acid of the polyamino acid used in the present invention may be one type of an amino acid or multiple types of amino acids. Thus, the polyamino acid used in the present invention may be comprised of one or more types of natural amino acids or one or more types of non-natural amino acids. Alternatively, it may be comprised of both of natural and non-natural amino acids. The non-natural amino acid refers to an amino acid other than naturally-occurring amino acids. The non-natural amino acids include chemically synthesized ones and ones formed by chemically modifying natural amino acids. Although the constituting amino acid may be L-form or D-form, it is preferably L-form. Thus, the polyamino acids of the present invention include modified forms and derivatives thereof. The terms "modified form" and "derivative" of the polyamino acid have the same meanings as those usually used in the art. Examples of the modified forms and derivatives of the polyamino acid of the present invention include a polyamino acid in which the constituting amino acids are partially substituted with other amino acids, and a polyamino acid modified using available functional groups on the constituting amino acids. Specific examples thereof include a polyamino acid in which one or more types of other amino acids (or modified forms or derivatives thereof) are introduced into a peptide chain of poly(γ-glutamic acid), a polyamino acid that forms a graft polymer, and a polyamino acid in which lysines constituting poly(ε-lysine) are partially methylated at the available α-positions. The type of the modified form or derivative of the polyamino acid of the present invention and a method for the preparation thereof can be readily selected and/or performed by the skilled person in the art.

Taking the safety or toxicity, in particular, the safety or toxicity (being nontoxic or less toxic) of the product generated by decomposition in a living body into consideration, the polyamino acid of the present invention is preferably biodegradable and composed of a natural amino acid. Preferable examples of the amino acids constituting the polyamino acid of the present invention include glutamic acid, aspartic acid, lysine, asparagine and arginine. Although the bonds between the constituting amino acids in the polyamino acid of the present invention are generally peptide bonds, the constituting amino acids may be bound via another bond or a linker. Examples of the bonds other than a peptide bond include, but are not limited to, an ester bond and an ether bond, and examples of the linkers include, but are not limited to, glutaraldehyde and diisocyanate. Furthermore, the functional groups on the polyamino acid of the present invention may be cross-linked. The cross-linking allows a physical property of the polyamino acid to be changed and to achieve the desired property as an adjuvant. Examples of cross-linkers include, but are not limited to, carbodiimide and diglycidyl ester. Although the polyamino acid is preferably soluble, it may be gradually dissolved over time. The molecular weight of the polyamino acid is not specifically limited, and can be changed depending on the desired viscosity or solubility. Usually, the molecular weight ranges from 1,000 to 5,000,000, preferably, from 5,000 to 2,000,000. The polyamino acids preferably used in the present invention include poly(γ-glutamic acid), poly(α-aspartic acid), poly(ε-lysine), poly(α-glutamic acid), poly(α-lysine) and polyasparagine. More preferably, the polyamino acid is poly(γ-glutamic acid) or poly(ε-lysine), or a modified form or a derivative thereof or a mixture thereof. Most preferably, the polyamino acid is poly(γ-glutamic acid). When preferable polyamino acid is selected, an interaction with the antigen used or another component should also be taken into consideration. Preferably, the polyamino acid used in the present invention is prepared as nanoparticles. The action as an adjuvant is increased by preparing as nanoparticles (see Example 1). For the preparation of the polyamino acid, a known method such as a chemical synthesis method or a fermentation method can be appropriately selected and used. A method for the preparation of the nanoparticle is set forth below.

In another aspect, the present invention relates to use of the polyamino acid as an adjuvant for the manufacture of a vaccine. The polyamino acid may be added in any step of the preparation of the vaccine. Alternatively, the vaccine may be prepared by mixing the polyamino acid with other components for the vaccine upon use. The components of the polyamino acid, the bond between the constituting amino acids, the preferable polyamino acid, the preferable form of the polyamino acid and the like are described above. The amount of the polyamino acid to be added can be appropriately adjusted depending on the type of the antigen, the type of the disease, the condition of the subject or the like. The vaccine to be prepared may be any one of the various types as described below. Because the ability of the polyamino acid as an adjuvant is high and the toxicity of the polyamino acid is absent or low, the vaccine obtained using the method of the present invention is highly effective and results in few side effects.

In another aspect, the present invention relates to a vaccine comprising the polyamino acid as an adjuvant. The component, the bond between the constituting amino acids, the preferable type and form and the like of the polyamino acid comprised in the vaccine of the present invention are described above. The vaccine of the present invention may comprise, for example, an excipient or a carrier, and optionally, a suspending agent, an isotonizing agent and a preservative in addition to the polyamino acid as an adjuvant and an antigen. The vaccine of the present invention may further comprise an adjuvant other than the polyamino acid of the present invention. The dosage form thereof is not specifically limited. The vaccine may be formulated in any form, and the formulation can be selected depending on various factors such as the condition of the subject or the type of the disease. It may be, for example, a suspension or a solution in a suitable aqueous carrier, or a powder, a capsule or a tablet. The vaccine may be in a lyophilized form, which is suspended or dissolved in a suitable excipient before use. The method, route and number of times of the administration of the vaccine of the present invention are not specifically limited, and they can be selected depending on various factors such as the dosage form, the condition of the subject or the type of the disease.

For example, the vaccine of the present invention may be administered via injection or infusion, or by oral administration. Alternatively, it may be administered locally to an affected area.

In the vaccine of the present invention, the antigen may or may not be immobilized to the polyamino acid. If the antigen is not immobilized, there is a very broad choice for the antigen. By appropriately selecting the antigen depending on factors such as the type of the disease or the condition of the subject, the desired vaccine can be readily prepared. The vaccine in which the antigen is immobilized is described below.

In one aspect, the present invention relates to a biodegradable nanoparticle to which an antigen is immobilized. An antigen means one that can elicit an immunoreaction. The form of the antigen may be, for example, a pathogen such as a virus (for example, human immunodeficiency virus (HIV)) or a pathogenic microorganism (for example, tuberculosis) or a part thereof, or it may be a protein or a peptide, or a nucleic acid. Preferably, the antigen used in the present invention is a virus antigen. The type of the antigen is not specifically limited, and any viral antigen may be used. For example, a retroviral antigen such as an HIV antigen (for example, HIV-1 antigen) or an HTLV antigen (for example, HTLV-1 antigen), an influenza viral antigen, a flaviviral antigen such as a hepatitis C viral antigen or a West Nile viral antigen, a diarrhea viral antigen such as a rotaviral antigen or a noroviral antigen, or an antigen of coronavirus such as a SARS virus is preferable. A retroviral antigen such as an HIV antigen or an HTLV antigen is more preferable, and an HIV antigen is most preferable. The antigen immobilized to the biodegradable nanoparticle of the present invention may be antigens of multiple types or different forms.

According to the present invention, immobilizing the antigen to the biodegradable nanoparticle means that the antigen and the biodegradable nanoparticle are physically linked to each other. Preferably, it means that the antigen is incorporated, or present on the surface of the particle. The immobilization of the antigen to the biodegradable nanoparticle can be performed by various known methods. The details thereof are described below.

As a material for the biodegradable nanoparticle used in the present invention, various materials can be used. The nanoparticle of the present invention is administered into a living body. Thus, it is preferable that the nanoparticle itself, or a decomposition product or a metabolite thereof is safe. Preferably, a main component (preferably, 50% by weight or more, without an immobilized antigen) of the biodegradable nanoparticle of the present invention is a polyamino acid. Preferably, the polyamino acid is poly(γ-glutamic acid), poly(α-aspartic acid), poly(ε-lysine), poly(α-glutamic acid), poly(α-lysine), polyasparagine or a mixture thereof. More preferably, it is poly(γ-glutamic acid). The bonds between amino acids that constitute such a polyamino acid may be identical to or different from each other. For example, all constituting amino acids may be bound via peptide bonds, or the amino acids may be bound partially or wholly via bonds other than peptide bonds. The amino acids may be bound via a linker. For the polyamino acid, see also the description about a polyamino acid as an adjuvant above.

Details of the type, composition, preparation method, shape, size and the like of the biodegradable nanoparticle are described below.

In another aspect, the present invention relates to a vaccine comprising the biodegradable nanoparticle to which an antigen is immobilized. The biodegradable nanoparticle obtainable as described above, to which an antigen is immobilized can be used as a vaccine. The antigen immobilized to the biodegradable nanoparticle can be appropriately selected to obtain various vaccines. Preferably, it is an anti-HIV vaccine comprising the biodegradable nanoparticle to which an HIV antigen is immobilized. In the vaccine of the present invention, the biodegradable nanoparticle is used as a support for the immobilization of the antigen or an adjuvant. Finally, it is decomposed by catabolic enzymes in a living body and made nontoxic or less toxic. The vaccine of the present invention comprises the biodegradable nanoparticle to which an antigen is immobilized, and an excipient or a carrier, and optionally, other components such as a suspending agent, an isotonizing agent and a preservative. Examples of the carriers or the excipients include an aqueous vehicle such as water, ethanol or glycerol, or a non-aqueous vehicle such as a fat or oil (for example, a fatty acid or a fatty acid ester). The vaccine of the present invention may be formulated in any form. The formulation can be selected depending on factors such as the condition of the subject or the type of the disease. It may be, for example, a suspension in a suitable aqueous carrier, or a powder, a capsule or a tablet. It may be a lyophilized vaccine, which is suspended in a suitable carrier or excipient before administration and used. The method, route and number of times of the administration of the vaccine of the present invention are not specifically limited, and they can be selected depending on factors such as the formulation, the condition of the subject or the type of the disease. For example, the vaccine of the present invention may be administered to the subject via injection or infusion, or by oral administration. Alternatively, it may be administered locally to an affected area.

Furthermore, by appropriately changing the material, component, molecular weight, size or other parameters of the biodegradable nanoparticle, the rate and time of release of the antigen can be controlled. The methods to do so are known in the art. For example, in case of the nanoparticle consisting of the graft copolymer of poly($\gamma$-glutamic acid) and a hydrophobic amino acid, a sustained-release vaccine can be obtained by controlling the type or content of the hydrophobic amino acid. For example, a bond which can be cleaved by an enzyme localized in a specific tissue or site may be introduced between the biodegradable nanoparticle and the immunogen or into the biodegradable nanoparticle to make the immunogen be released in the specific tissue or site.

The vaccine of the present invention can be administered to various subjects for the purpose of preventing and treating various diseases. The disease and the administered subject to which the vaccine of the present invention can be applied are not specifically limited. Such prevention and treatment may be performed, for example, by making an antigen-presenting cell (APC) present the antigen along with an MHC class I molecule, inducing a CTL that recognizes specifically it, and damaging a cancer cell, an infected cell or the like by using the CTL. Thus, the diseases prevented and treated according to the present invention include malignant tumors, and infections caused by pathogens such as viruses or bacteria. The malignant tumors include breast cancer, lung cancer, gastric cancer, colon cancer, hepatic cancer, ovarian cancer, bladder cancer, leukemia and malignant melanoma. The infections include adult T cell leukemia, hepatitis and acquired immunodeficiency syndrome. For example, the vaccine of the present invention can be used to treat adult T cell leukemia (see Example 8).

The present invention also provides a method for the immunization of a subject, comprising administering the vaccine comprising the biodegradable nanoparticle to which a virus antigen is immobilized to the subject. By appropriately selecting the viral antigen immobilized to the biodegradable nanoparticle which is contained in the vaccine of the present invention, it is possible to induce an immunoreaction such as induction of a CTL or an antibody specific for the viral antigen in the subject. The method, route, number of times or the like of the administration of the vaccine of the present invention can be appropriately selected depending on various factors such as the condition of the subject or the type of the viral antigen.

The present invention also provides a method for the treatment and/or prevention of a disease in a subject, comprising administering the vaccine comprising the biodegradable nanoparticle to which a virus antigen is immobilized to the subject. By appropriately selecting the viral antigen immobilized to the biodegradable nanoparticle which is comprised in the vaccine of the present invention, it is possible to treat and/or prevent a wide range of diseases including, for example, acquired immune deficiency syndrome, human T cell leukemia, retrovirus infection, influenza, hepatitis C, West Nile virus infection, rotavirus infection, norovirus infection and SARS as well as various tumors. The method, route, number or times or the like of the administration of the vaccine of the present invention can be appropriately selected depending on various factors such as the condition of the subject, the type of the disease or the type of the viral antigen.

The present invention further relates to use of the biodegradable nanoparticle to which a virus antigen is immobilized for the manufacture of the vaccine for the treatment and/or prevention of a disease. By appropriately selecting the viral antigen immobilized to the biodegradable nanoparticle, it is possible to manufacture the vaccines for the treatment and/or prevention of various diseases such as those described above.

The present invention further relates to use of the biodegradable nanoparticle to which a virus antigen is immobilized for the manufacture of the vaccine for the immunization of a subject. By appropriately selecting the viral antigen immobilized to the biodegradable nanoparticle, it is possible to manufacture the vaccine that induces an immunoreaction specific for the viral antigen in the subject.

In another aspect, the present invention relates to a biodegradable nanoparticle to which an antigen is immobilized. Various materials can be used for the biodegradable nanoparticle used in the present invention. Such materials are well known in the art, and can be appropriately selected and used. The nanoparticle of the present invention is administered into a living body. Thus, it is preferable that the nanoparticle itself, or a decomposition product or a metabolite thereof is safe, or nontoxic or less toxic. Examples of such preferable materials include polypeptides, polysaccharides, polyorganic acids and mixtures thereof.

A biodegradable nanoparticle whose main material is a polypeptide (referred to as a "biodegradable polypeptide nanoparticle") may have as its backbone a polyamino acid comprising natural amino acids, modified amino acids (for example, an esterified amino acid), amino acid derivatives, synthetic amino acids or mixtures thereof. In view of the safety or toxicity, a polyamino acid consisting of natural amino acids is preferable. Examples of such preferable polyamino acids consisting of natural amino acids include poly($\gamma$-glutamic acid), poly $\epsilon$-lysine, poly($\alpha$-L-lysine), poly ($\alpha$-aspartic acid), poly($\alpha$-glutamic acid), polyasparagine, as well as modified forms and derivatives thereof. The terms "modified amino acid", "amino acid derivative", "modified form" and "derivative" have the same meanings as those usually used in the art. The biodegradable polypeptide nanoparticle may consist of a single type of amino acid or two or more types of amino acids. In the biodegradable polypeptide nanoparticle, bonds between all constituting amino acids may be identical to or different from each other. For example, all constituting amino acids may be bound via peptide bonds, or the amino acids may be bound partially or wholly via bonds other than peptide bonds. The amino acids may be bound via linkers. For example, it is possible to achieve a desired balance between hydrophilicity and hydrophobicity by introducing a hydrophobic amino acid into a side chain of a hydrophilic polyamino acid. For example, the polypeptide may be a graft polymer consisting of γ-glutamic acid and phenylalanine ethyl ester. The biodegradable polypeptide nanoparticle of the present invention comprises a polypeptide as its main component (preferably, 50% by weight or more, without an immobilized antigen). Preferably, it has a polypeptide as its backbone. The biodegradable polypeptide nanoparticle of the present invention may or may not comprise a component other than a polypeptide or an amino acid in its backbone or another moiety. For the biodegradable polypeptide of the present invention, also see the description about a polyamino acid as an adjuvant above.

A biodegradable nanoparticle whose main material is a polysaccharide (referred to as a "biodegradable polysaccharide nanoparticle") may comprise a natural polysaccharide, a modified polysaccharide, a polysaccharide derivative, a synthetic polysaccharide or a mixture thereof. In view of the safety or toxicity, it preferably consists of a natural polysaccharide. Examples of such preferable biodegradable nanoparticles consisting of a natural polysaccharide include those consisting of pullulan, chitosan, alginic acid, pectin, curdlan and dextran. The terms "modified polysaccharide" and "polysaccharide derivative" have the meanings usually used in the art. The biodegradable polysaccharide nanoparticle may consist of a single type of saccharide or two or more types of saccharides. Furthermore, in the biodegradable polysaccharide nanoparticle, all constituting saccharides may be bound via the same type of bonds, or the constituting saccharides may be bound partially or wholly via different types of bonds. For example, there may be both α-1,6 bonds and α-1,4 bonds. The saccharides may also be bound via linkers. The biodegradable polysaccharide nanoparticle of the present invention comprises a polysaccharide as its main component (preferably, 50% by weight or more, without an immobilized antigen). Preferably, it has a polysaccharide as its backbone. The biodegradable polysaccharide nanoparticle of the present invention may or may not comprise components other than a saccharide in its backbone or another moiety.

A biodegradable nanoparticle whose main material is a polyorganic acid (for a polypeptide, see above) (referred to as a "biodegradable polyorganic acid nanoparticle") may be composed of a natural polyorganic acid, a modified polyorganic acid, a polyorganic acid derivative, a synthetic polyorganic acid or a mixture thereof. In view of the safety or toxicity, it preferably consists of a natural polyorganic acid. Examples of such preferable biodegradable nanoparticles consisting of a natural polyorganic acid include a polylactic acid nanoparticle, a polyglycolic acid nanoparticle and a polycaprolactone nanoparticle. The terms "modified polyorganic acid" and "polyorganic acid derivative" have the same meanings as those usually used in the art. The biodegradable polyorganic acid nanoparticle may consist of a single type of organic acid or two or more types of organic acids. Furthermore, in the biodegradable polyorganic acid nanoparticle, the organic acids may be bound via the same type of bonds, or the organic acids may be bound partially or wholly via different types of bonds. The organic acids may be bound via linkers. The biodegradable polyorganic acid nanoparticle of the present invention comprises a polyorganic acid as its main component (preferably, 50% by weight or more, without an immobilized antigen). Preferably, it has a polyorganic acid as its backbone. The biodegradable polyorganic acid nanoparticle of the present invention may or may not comprise components other than a polyorganic acid or an amino acid in its backbone or another moiety.

Although the form of the biodegradable nanoparticle used in the present invention is not specifically limited, in general, the biodegradable nanoparticle is spherical. Its size is usually 100 nm-10 μm, preferably, 100 nm-500 nm. Such size brings an effect such as an increase in the amount of an immobilized antigen resulting from an increase in the surface area of a particle per unit weight, promotion of incorporation an antigen into an antigen-presenting cell which results in activation of a CTL, or induction of antibody production. For a nanoparticle in a form other than a spherical form, the preferable size follows that of a spherical nanoparticle.

The biodegradable nanoparticle used in the present invention can be prepared by applying a known method. For the preparation of the biodegradable polypeptide nanoparticle, for example, drying-in-liquid method, spray drying method, spherical crystallization method, solvent replacement method (precipitation or dialysis) or direct ultrasonic dispersion method can be used. For example, a biodegradable nanoparticle consisting of poly(γ-glutamic acid) or poly(ε-lysine) can be prepared by solvent replacement method. For the preparation of the biodegradable polysaccharide nanoparticle, for example, direct dispersion method can be used. For the preparation of the biodegradable polyorganic acid nanoparticle, for example, emulsion-drying-in-liquid method can be used. By appropriately selecting or combining such method(s), the material, component, molecular weight, size, charge or other parameters for the biodegradable nanoparticle can be made suitable for the purpose. Furthermore, optionally, matrices binding the nanoparticles may be cross-linked.

As an antigen which is immobilized to the biodegradable nanoparticle, various antigens can be used. The antigen may be, for example, a protein or a peptide, or a nucleic acid, or it may be a pathogen such as a virus, a bacterium or a fungus, or a part thereof. For example, a tumor antigen may be immobilized to the biodegradable nanoparticle. Depending on the condition of the subject to be administered such as the animal specie, age, weight, health condition, or type of the disease to be prevented and/or treated (for example, the disease from which the subject is suffering or the predisposition of the subject), an antigen can be appropriately selected and immobilized to the biodegradable nanoparticle. One type of antigen or two or more types of antigens may be immobilized to the biodegradable nanoparticle.

Immobilization of the antigen to the biodegradable nanoparticle can be performed by various known methods. For example, binding method via a covalent bond or an ionic bond, or by intermolecular force, adsorption method, entrapment method and the like are known. For example, the antigen may be immobilized via a covalent bond between a functional group on the biodegradable nanoparticle and a functional group on the antigen. Alternatively, the antigen may be immobilized via an ionic bond if the charge of the biodegradable nanoparticle is contrary to the charge of the antigen. According to entrapment method, for example, a proteinous antigen can be immobilized to poly(γ-glutamic acid) biodegradable nanoparticle by introducing a hydrophobic amino acid into the poly(γ-glutamic acid) via a covalent bond, dissolving the product in an organic solvent, and then dropping the solution into an aqueous solution of the antigen. Furthermore, binding method, adsorption method and/or entrapment method may be appropriately combined to immobilize the antigen to the biodegradable nanoparticle. Thus, the antigen may be incorporated into the biodegradable nanoparticle, or it may be present on the surface of the biodegradable nanoparticle. Such a mode of immobilization can be appropriately selected according to the purpose of use of the vaccine (for example, the subject or the type of the disease). In the biodegradable nanoparticle to which the antigen is immobilized of the present invention, the conformation of the antigen is not influenced by the binding with the biodegradable nanoparticle or by the incorporation into the biodegradable nanoparticle. It is advantageous in that, for example, the quantity or quality of the protein immobilized is not changed even after lyophilization, and it can be stored for a long period.

In a further aspect, the present invention relates to use of a biodegradable nanoparticle to which an antigen is immobilized for the manufacture of a vaccine.

In another aspect, the present invention relates to a method for the immunization of a subject, comprising administering to the subject the vaccine comprising a biodegradable nanoparticle to which an antigen is immobilized. The material for the biodegradable nanoparticle and the like are described above. By appropriately selecting the antigen immobilized to the biodegradable nanoparticle which is comprised in the vaccine of the present invention, an immunoreaction such as induction of a CTL or an antibody specific for the antigen can be induced in the subject. For example, a pathogen such as a virus or a part thereof can be used as an antigen to generate immunity to various infections in the subject. Furthermore, for example, when the vaccine comprising the biodegradable nanoparticle to which a tumor antigen is immobilized is used, an immunoreaction specific for the tumor is induced in the subject. The method, route, number of times or the like of the administration of the vaccine of the present invention can be appropriately selected depending on various factors such as the condition of the subject or the type of the antigen.

In another aspect, the present invention relates to a method for the treatment and/or prevention of a disease in a subject, comprising administering to the subject the vaccine comprising the biodegradable nanoparticle to which an antigen is immobilized. The material for the biodegradable nanoparticle and the like are described above. By appropriately selecting the antigen immobilized to the biodegradable nanoparticle which is comprised in the vaccine of the present invention, a wide range of diseases can be prevented and/or treated. For example, a pathogen such as a virus or a part thereof can be used as an antigen to treat and/or prevent various infections in the subject. For example, by using the vaccine comprising the biodegradable nanoparticle to which a tumor antigen is immobilized, the tumor can also be treated and/or prevented in the subject. The method, route, number of times and the like of the administration of the vaccine of the present invention can be appropriately selected depending on various factors such as the condition of the subject, the type of the disease or the type of the antigen.

In another aspect, the present invention relates to use of the biodegradable nanoparticle to which an antigen is immobilized for the manufacture of a vaccine for the treatment and/or prevention of a disease. The material for the biodegradable nanoparticle and the like are described above. By appropriately selecting the antigen immobilized to the biodegradable nanoparticle, it is possible to manufacture the vaccine which induces an immunoreaction specific for the antigen in the subject.

The present invention further provides use of a biodegradable nanoparticle as a carrier. As used herein, the carrier means a material that can transport a substance such as an antigen to a desired site. By appropriately selecting the size of the biodegradable nanoparticle depending on, for example, a tissue or cell of interest, an effect of the biodegradable nanoparticle as a carrier can be increased. It is known that an antigen-presenting cell has a property to uptake effectively a particulate substance with 50 nm-3 μm in diameter. Therefore, for example, the size of the biodegradable nanoparticle of the present invention may be adjusted to such size. Since the nanoparticle of the present invention is biodegradable, it is advantageous in that it is nontoxic or less toxic to a living body. The material for the biodegradable nanoparticle, the preferable polyamino acid and the like are described above.

The present invention further provides a pharmaceutical composition comprising the biodegradable nanoparticle as a carrier. The pharmaceutical composition of the present invention may be any one as long as it comprises the biodegradable nanoparticle. The material for the biodegradable nanoparticle, the preferable polyamino acid and the like are described above.

The present invention further provides use of the biodegradable nanoparticle as a carrier for the manufacture of the pharmaceutical composition. Any substance may be comprised in the pharmaceutical composition. For example, an antigen such as a tumor antigen or a virus antigen may be comprised, or a substance for which an effect of activating an antigen-presenting cell is known may be comprised. The material for the biodegradable nanoparticle, the preferable polyamino acid and the like are described above.

The following examples illustrate the present invention in more detail, but are not to be construed to limit the scope thereof. In the examples, poly(γ-glutamic acid) is abbreviated as γ-PGA.

EXAMPLE 1

Adjuvant Action of γ-PGA

Bone marrow cells were isolated from a mouse lower limb, and cultured in the presence of GM-CSF to obtain immature dendritic cells (iDCs). The iDCs were then cultured in the medium containing 100 μg/ml of γ-PGA or 100 μg/ml of γ-PGA nanoparticles (size; 177 nm) for 2 days. The resulting cells were cocultured with T-lymphocytes from an allogeneic mouse for 3 days. After the culture, the T-lymphocytes were incubated with $^3$H-thymidine for 16 hours. By measuring the incorporated amounts, it was examined whether or not the γ-PGA and γ-PGA nanoparticle induce differentiation of iDCs into mature dendritic cells (mDCs), and these mDCs activate T-lymphocytes. As a negative control, the iDCs which had been cultured in the medium without γ-PGA were used. The results are represented as values defining the amount of $^3$H-thymidine incorporation in the negative control as 100 (%) (FIG. 1). It was found that: γ-PGA increases the amount of $^3$H-thymidine incorporation into T-lymphocytes, that is, it allows iDCs to differentiate and mature into mDCs; the mDCs activate T-lymphocytes; and this action (i.e., adjuvant action) is enhanced by preparing γ-PGA as a nanoparticle.

EXAMPLE 2

Promotion of Differentiation and Maturation of Dendritic Cell (DC) by γ-PGA Nanoparticle A. Increase in Expression of Surface Molecule on DC by γ-PGA Nanoparticle The iDCs obtained according to the method of Example 1 were cultured in the medium containing 75, 150 or 300 μg/ml of γ-PGA nanoparticles for 2 days. After the culture, the cell surface molecules, of which expression is increased as DCs differentiate and mature (CD40, CD80, CD86, MHC class I and MHC class II), were measured using a flow cytometer. The iDCs which had been cultured in the medium without a γ-PGA nanoparticle were used as a negative control, and mDCs obtained by culturing iDCs in the medium containing LPS (lipopolysaccharide), which is known as a differentiation-inducing agent for DCs, were used as a positive control. It was found that the γ-PGA nanoparticle can increase the expression of CD40, CD86 and MHC class I in a concentration-dependent manner, that is, it can induce the differentiation of iDCs into mDCs and activate them (see FIG. 2).

B. Increase in Amount of Cytokine Production in DC by γ-PGA Nanoparticle

Figure 3:
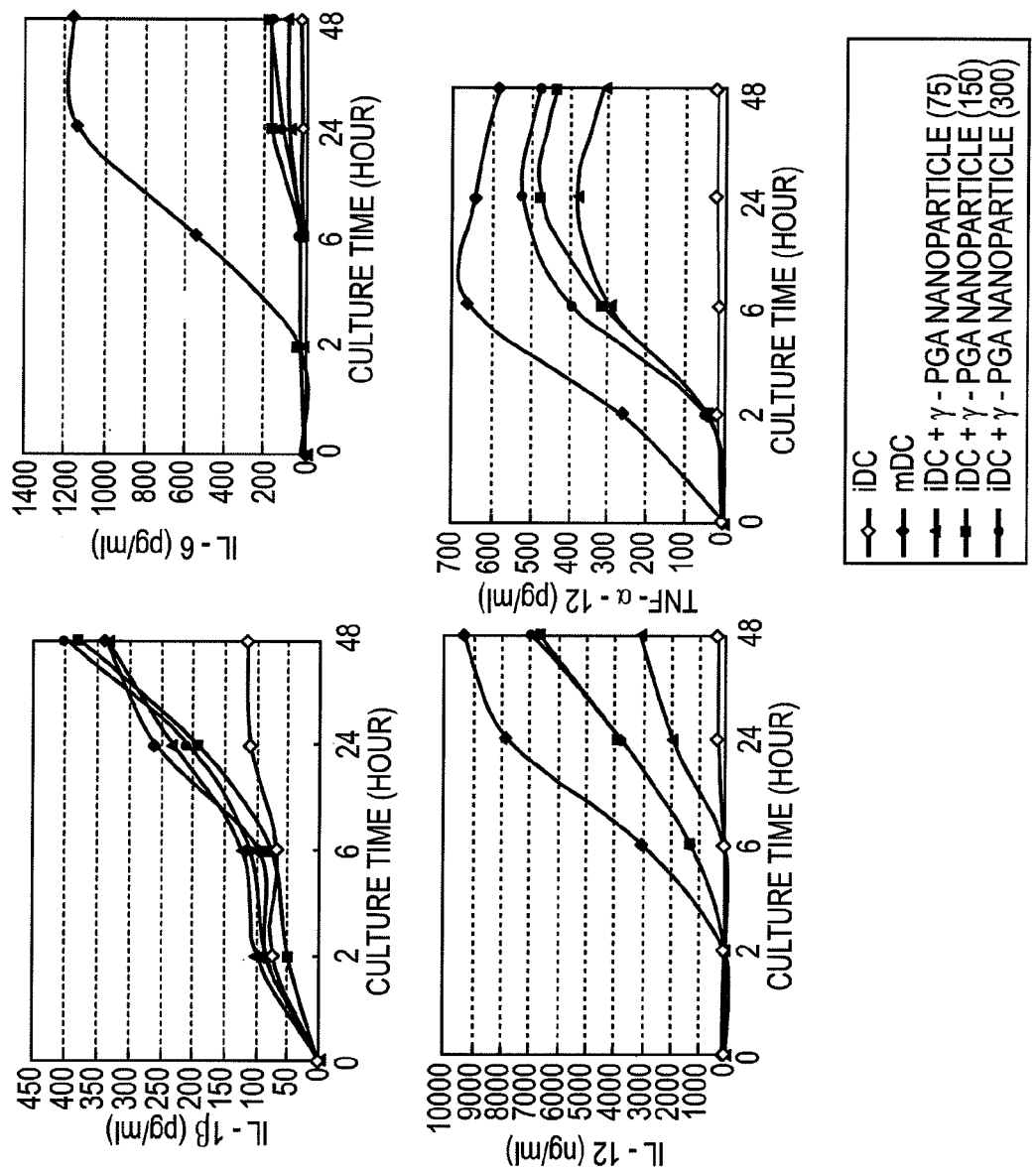
FIG. 3 is a graph which represents amounts of cytokines secreted from dendritic cells, which are measured by ELISA.

The iDCs obtained according to the method of Example 1 were incubated with γ-PGA nanoparticles (75, 150 or 300 µg/ml). After the incubation for 2, 6, 24 or 48 hours, culture supernatants were collected. The cytokines (IL-1β, IL-6, IL-12 and TNF-α) produced and secreted from the DCs were quantified by ELISA. The iDCs which had been incubated in the medium without a γ-PGA nanoparticle for the same period of time were used as a negative control, and the mDCs obtained by incubating the iDCs with LPS for the same period of time were used as a positive control. It was found that the γ-PGA nanoparticle increases the production amounts of IL-1β, IL-12 and TNF-α (see FIG. 3). Furthermore, it was found that the increases in the production amounts of IL-12 and TNF-α are enhanced in a manner dependent on the concentration of the γ-PGA nanoparticle. It was confirmed that the γ-PGA nanoparticle induces the differentiation of iDCs into mDCs and activates them, because the production amounts of these cytokines are increased as DCs differentiate and mature.

EXAMPLE 3

T-Lymphocyte Activation Action of iDC Differentiation-Induced by γ-PGA Nanoparticle According to the method of Example 1, the iDCs were differentiated by culturing in the medium containing γ-PGA nanoparticles (75, 150 or 300 µg/ml) for 2 days. The resulting cells were then cocultured with T-lymphocytes from an allogeneic mouse for 4 days. After the culture, T-lymphocytes were incubated with $^3$H-thymidine for 16 hours. By measuring the amounts of its incorporation, the T-lymphocyte activation action of the differentiated iDCs was examined. The iDCs which had been cultured in the medium without a γ-PGA nanoparticle were used as a negative control, and mDCs obtained by differentiating and maturing with LPS were used as a positive control. It was confirmed that the amounts of $^3$H-thymidine incorpororation into T-lymphocytes are increased in a manner dependent on the concentration of γ-PGA nanoparticle used for differentiation of the iDCs, that is, T-lymphocyte activation action by γ-PGA nanoparticle is enhanced in a concentration-dependent manner (see FIG. 4).

EXAMPLE 4

Induction of γ-Interferon-producing Cell by γ-PGA Nanoparticle Having Incorporated HIV-1 Antigen (p24)

Figures 4, 5:
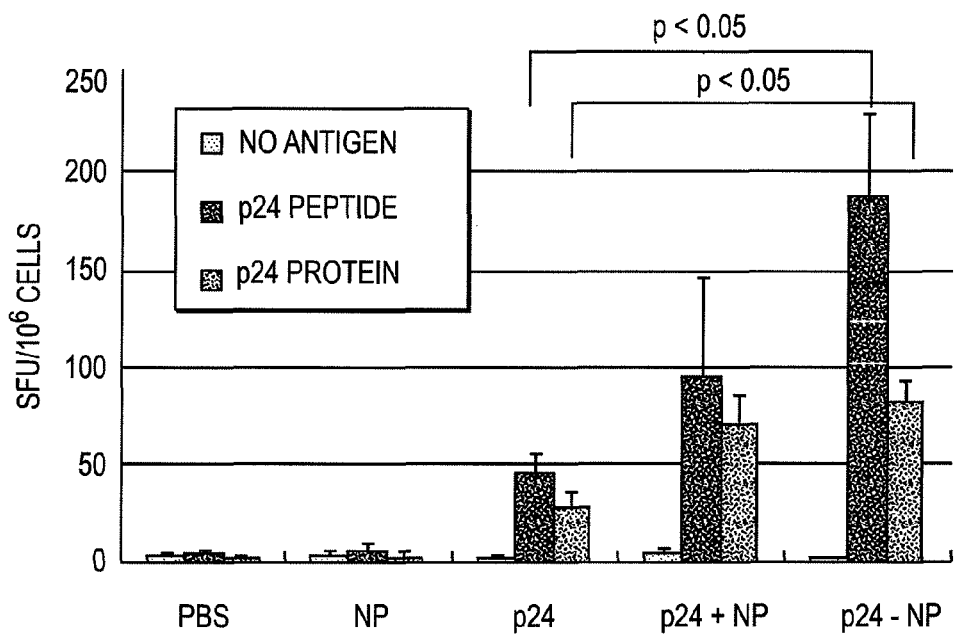
FIG. 4 shows effects of iDCs differentiated by γ-PGA nanoparticles on T-lymphocyte activation, which is represented by amounts of $^3$H-thymidine incorporation into T-lymphocytes.
FIG. 5 is a graph which represents the number of γ-interferon producing cells induced by γ-PGA nanoparticles having an HIV-1 antigen incorporated therein.

6- to 8-week-old female BALB/c(H-2d) mice were immunized with the γ-PGA having an incorporated p24 antigen (p24–NP) three times at intervals of 7 days. As controls, PBS (negative control), the γ-PGA nanoparticle (NP) alone, the p24 antigen (p24) alone, and the mixture of the p24 antigen and the γ-PGA nanoparticle (p24+NP) were used. The amounts of the γ-PGA nanoparticle and the p24 antigen used were 1 mg and 25 µg per immunization, respectively. On day 10 after the final immunization, cells were harvested from spleens, and incubated with 10 mg/ml of p24 peptide (AMQMLKETI (SEQ ID No: 1)) or 10 mg/ml of recombinant p24 protein for 24 hours. The numbers of the p24-specific IFN-γ-producing cells were determined by ELISPOT assay (BD Bioscience). All data are represented using the average numbers of formed spots per 1×10$^6$ cells (SFU) ±SE. The statistical significances were analyzed using t-test. The results are shown in FIG. 5. It was found that more IFN-γ-producing cells are induced in the group of the immunization with p24–NP than in the groups of the immunization with p24 alone and p24+NP.

EXAMPLE 5

Induction of Antigen-specific Antibody by γ-PGA Nanoparticle Having Incorporated HIV-1 Antigen (p24)

Figure 6:
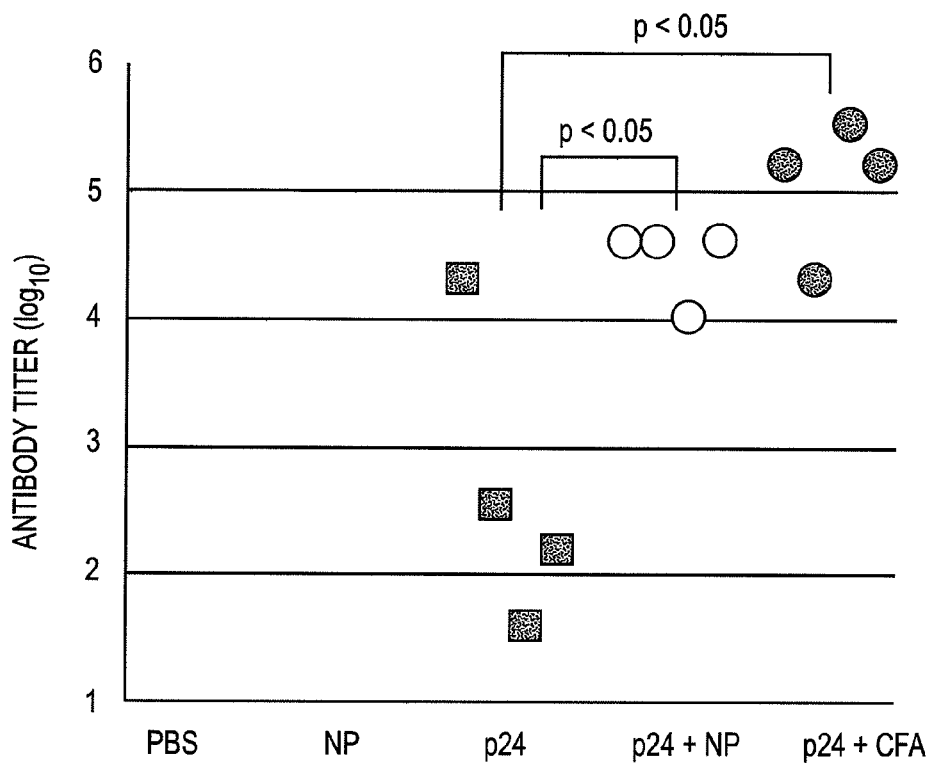
FIG. 6 is a graph which represents titers of antibodies induced by γ-PGA nanoparticles having an HIV-1 antigen incorporated therein.

6- to 8-week-old female BALB/c(H-2d) mice were immunized with the γ-PGA nanoparticles having an incorporated p24 antigen (p24–NP) twice at intervals of two weeks (n=4). As controls, PBS (negative control), the γ-PGA nanoparticle (NP) alone, the p24 antigen (p24) alone and the mixture of the p24 antigen and complete Freund's adjuvant (p24+CFA) were used. The amounts of the γ-PGA nanoparticle and the p24 antigen used were 1 mg and 25 µg per immunization, respectively. On day 10 after the final immunization, blood was collected, and the levels of the antigen-specific antibody contained in the sera were measured. The final antibody titer is represented as an inverse of the final dilution rate which results in a higher absorbance (450 nm) by 2SDs (about 0.1) than that for a non-immunized mouse. The statistical significances were analyzed using t-test. The results are shown in FIG. 6. It was found that the antibody titers in the sera of the group of the immunization with p24–NP are much higher as compared with those in the group of the immunization with p24 alone. Furthermore, these values are compatible with those in the group of the immunization with CFA which is a known adjuvant (p24+CFA).

The results of Examples 4 and 5 reveal that the effectiveness of the vaccine comprising the biodegradable nanoparticle to which an antigen is immobilized, of the present invention, in particular, the anti-HIV vaccine. It was further confirmed that the γ-PGA nanoparticle has an effect as an adjuvant.

EXAMPLE 6

Experiment for Preventing Tumor Growth Engraftment by OVA-immobilized γ-PGA (Poly(γ-Glutamic Acid)) Nanoparticle A. Materials C57/BL6 mice (female, 6-week-old) were purchased from Japan SLC, Inc., and complete Freund's adjuvant was purchased from Wako Pure Chemical Industries, Ltd. EG7 cells which express OVA were purchased from American Type Culture Collection, and cultured using complete RPMI 1640 medium (SIGMA) containing 400 µg/ml of G418 (Wako Pure Chemical Industries, Ltd.).

B. Methods 607 mg (4.7 unit mmol) of γ-PGA (molecular weight 300,000) was dissolved in 100 ml of 54 mM $NaHCO_3$ aqueous solution (pH 8.5). 901 mg (4.7 mmol) of 1-ethyl-3-(3-dimethylaminopropyl)carbodiimide hydrochloride (WSC) and 1080 mg (4.7 mmol) of L-phenylalanine ethyl ester (L-PAE) were then added, and reacted at room temperature overnight with stirring. After the reaction, the resulting solution was dialyzed against water for 3 days using a dialysis membrane (fractionation molecular weight 50,000) and lyophilized. The resulting lyophilizate was added to 100 ml of ethanol and stirred overnight. The resulting solution was centrifuged (1,500×g, 20 minutes). The precipitate was dried under a reduced pressure to obtain γ-PGA-g-L-PAE. 100 mg of γ-PGA-g-L-PAE was dissolved in 10 ml of DMSO at a concentration of 10 mg/ml. Equal volumes (1 ml) of 10 mg/ml γ-PGA-g-L-PAE and 2 mg/ml OVA (SIGMA) solutions were mixed and reacted. After the reaction, the mixture was centrifuged at 14,000×g for 15 minutes. The supernatant was removed, and the precipitate was redispersed in PBS. This procedure was repeated to eliminate the unreacted OVA. Finally, 10 mg/ml OVA-incorporated γ-PGA nanoparticle was prepared. It was found that γ-PGA in the amphiphilic form can conveniently, effectively and homogenously incorporate the protein of interest only by dispersing it in a solution of the protein.

100 μl of samples comprising 100 μg and 10 μg of OVA were subcutaneously injected to immunize mice. Complete Freund's adjuvant (CFA) was mixed with an equal volume of 2 mg/ml OVA protein solution well to obtain an emulsion. The emulsion was used as a control. One week after the immunization, EG7 cells were inoculated at $1 \times 10^6$ cells/50 μl per mouse by intradermal injection into abdomen. After the inoculation of EG7 cells, diameters of tumors were measured over time, and tumor volumes were calculated according to the following equation;

(tumor volume: $mm^3$)=(longer diameter of tumor: mm)×(shorter diameter of tumor: $mm)^2$×0.5236

C. Results

Figure 7:
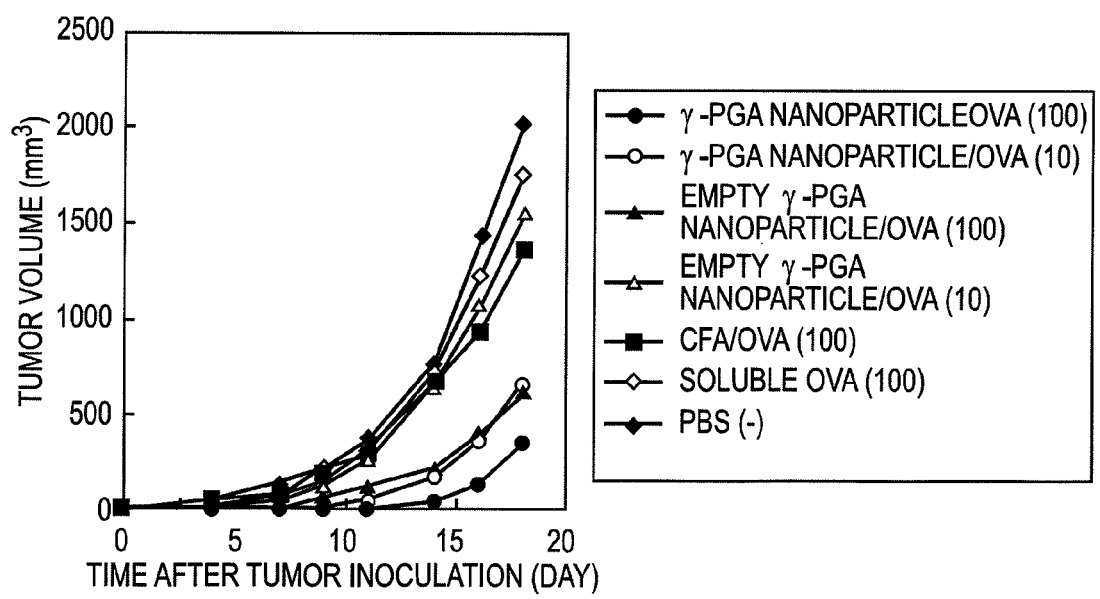
FIG. 7 represents results of experiments for preventing experiments for preventing tumor engraftment using OVA-immobilized γ-PGA nanoparticles.

As shown in FIG. 7, remarkable delay in the tumor growth was confirmed in the groups of the immunization with OVA-incorporated γ-PGA nanoparticles (γ-PGA/OVA nanoparticle (100) and (10)) as compared with the group of the immunization with PBS. Slight delay in tumor engraftment was observed in the groups of the immunization with γ-PGA nanoparticles without OVA and the immunization with OVA (empty γ-PGA nanoparticle/OVA (100) and (10)). It is considered that this is caused by the incorporation of OVA absorbed on the surface of the γ-PGA nanoparticle into antigen-presenting cells. These results show that the γ-PGA nanoparticle has a property of being readily incorporated into an antigen-presenting cell. Furthermore, the OVA-incorporated γ-PGA nanoparticles obtained in this example exhibit a stronger antitumor effect than that in the group of the immunization with complete Freund's adjuvant (CFA/OVA (100)) which is currently known to have the strongest ability to induce CTLs at the animal experimental level. It was confirmed that the OVA-incorporated γ-PGA nanoparticles obtained in this example can be stored in a lyophilized state and do not have cytotoxicity. Therefore, it was revealed that the OVA-incorporated γ-PGA nanoparticle fully meets the requirements as a carrier and an adjuvant for a vaccine.

EXAMPLE 7

Experiment for Inducing CTL Using OVA-immobilized γ-PGA Nanoparticle

A. Materials

EL4 cells which express OVA were provided by Cancer Cell Repository, Institute of Development, Aging and Cancer, Tohoku University and cultured using complete RPMI 1640 medium (SIGMA) containing $5 \times 10^{-5}$ M 2-mercaptoethanol (Invitrogen), 100 U/ml of penicillin, 100 μg/ml of streptomycin (Wako Pure Chemical Industries, Ltd.) and 10% fetal bovine serum (FBS). Mitomycin C was purchased from Wako Pure Chemical Industries, Ltd., recombinant mouse IL-2 was purchased from Peprotech, and $Na_2^{51}CrO_4$ was purchased from Amersham Bioscience. C57/BL6 mice, complete Freund's adjuvant and EG7 cells are described in Example 6.

B. Methods

OVA-incorporated γ-PGA nanoparticles were prepared as described in Example 6. The immunization of mice was performed by injecting subcutaneously 100 μl of sample comprising 100 μg or 25 μg of OVA. On day 10 after the immunization, splenocytes were passed through nylon meshes to disengage them into single cells, and mononuclear cells were harvested. Mononuclear cells ($4 \times 10^6$ cells/ml) harvested from each immunized mouse were cocultured with EG7 ($4 \times 10^5$ cells/ml) that had been treated with 30 μg/ml of mitomycin C for 30 minutes in complete RPMI 1640 medium containing 10 U/ml of mouse IL-2 for 5 days (37° C., 5% $CO_2$) to prepare effector cells. As target cells, EL4 cells and EG7 cells labeled with $Na_2^{51}CrO_4$ (0.56 MBq/$10^6$ cells, 37° C., 1 hour) were used. Target cells were added to a 96-well plate at the concentration of $10^4$ cells/well, and effector cells were then added at the concentration of 12.5, 25, 50 or 100× $10^4$ cells/well. They were incubated at 37° C. for 4 hours, and $^{51}Cr$ activities in the supernatants were measured. CTL activities were calculated according to the following equation:

Lysis (%)=100×{($^{51}Cr$ release with effector cells)−(Spontaneous $^{51}Cr$ release)}/{(Maximum $^{51}Cr$ release)−(Spontaneous $^{51}Cr$ release)}.

C. Results

Induction of OVA-specific CTLs was observed in spleens of mice immunized with γ-PGA nanoparticles (FIG. 8(a) and (b)). They exhibited stronger antitumor effects than those in the group of the immunization with CFA/OVA (FIG. 8(d)). In the group of the immunization with OVA alone, no CTL activity was observed (FIG. 8(e)). In the empty γ-PGA nanoparticle/OVA group (FIG. 8(c)), a slight CTL activity was found. It is considered that this is caused by the incorporation of OVA absorbed on the surface of the γ-PGA nanoparticle into antigen-presenting cells. These results show that a γ-PGA nanoparticle which is biodegradable has a property of being readily incorporated into an antigen-presenting cell and a very excellent ability as a carrier and an adjuvant for a CTL-inducing antigen.

EXAMPLE 8

Experiment for Inducing CTL Using $Tax_{38-46}$-immobilized γ-PGA Nanoparticle

A. Materials

C3H/HeJ mice (female, 6-week-old) were purchased from Japan SLC, Inc. Mouse fibroblasts (L929) were purchased from ATCC, and cultured using complete MEM medium (SIGMA) containing 100 U/ml of penicillin, 100 μg/ml of streptomycin (Wako Pure Chemical Industries, Ltd.) and 10% fetal bovine serum (FBS). $Tax_{38-46}$ peptide was purchased from SIGMA Genosys. Complete Freund's adjuvant and $Na_2^{51}CrO_4$ are described above.

B. Methods

γ-PGA nanoparticles having incorporated $Tax_{38-46}$ peptide which is a mouse $H-2K^K$-restricted epitope of human T cell leukemia virus (HTLV-1) were prepared as described in Example 6. The immunizations of mice were performed by injecting subcutaneously 100 μl of sample containing 100 pmol or 10 pmol of $Tax_{38-46}$ peptide three times at intervals of one week. On day 10 after the final immunization, mononuclear cells were harvested as described in Example 7. Mononuclear cells ($1 \times 10^7$ cells/ml) were treated with 30 μg/ml of mitomycin C for 30 minutes, and mixed with L929 cells acted with 1 μM $Tax_{38-46}$ peptide ($2.5 \times 10^6$ cells/ml) at the ratio of 4:1. They were cocultured in complete RPMI 1640 medium containing 10 U/ml of mouse IL-2 for 5 days (37° C., 5% $CO_2$) to prepare effector cells. As target cells, L929 cells which had been reacted with 1 μM $Tax_{38-46}$ peptide and labeled with $Na_2{}^{51}CrO_4$ ($0.56 MBq/10^6$ cells, 37° C., 1 hour) were used. Target cells were added to a 96-well plate at the concentration of $10^4$ cells/well, and effector cells were then added at the concentrations of 12.5, 25, 50 or $100 \times 10^4$ cells/well. They were incubated at 37° C. for 4 hours, and $^{51}Cr$ activities in the supernatants were measured. CTL activities were calculated according to the following equation:

Lysis (%)=100×{($^{51}$Cr release with effector cells)−(Spontaneous $^{51}$Cr release)}/{(Maximum $^{51}$Cr release)−(Spontaneous $^{51}$Cr release)}.

C. Results

Figure 9A:
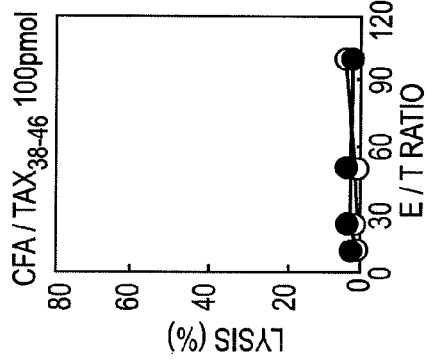
FIG. 9 represents results of experiments for inducing CTL induction by Tax$_{38-46}$-immobilized γ-PGA nanoparticles.
Figure 9B:
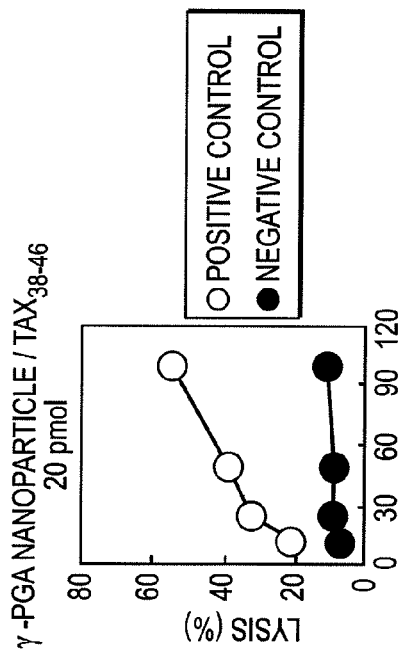
Figure 9C:
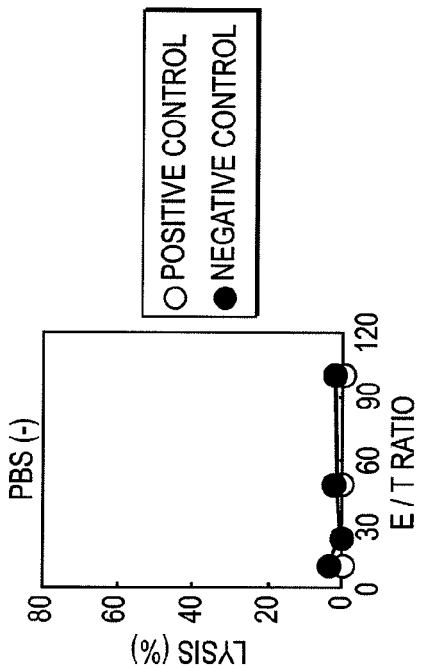
Figure 9D:
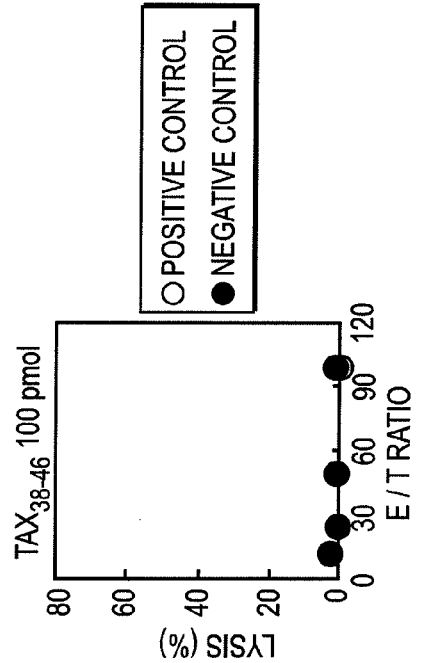

As shown in FIG. 9(a), induction of $Tax_{38-46}$-specific CTLs was observed in spleens of mice immunized with γ-PGA nanoparticles as compared with that in the group of the immunization with PBS (FIG. 9(d)). These were stronger antitumor effects than those in the group of the immunization with CFA/$Tax_{38-46}$ (FIG. 9(b)). In the group of the immunization with $Tax_{38-46}$ alone, no CTL activity was observed (FIG. 9(c)). $Tax_{38-46}$-immobilized nanoparticles obtained in this example have a property or characteristic similar to those obtained in Examples 6 and 7.

EXAMPLE 9

Test for Suppressing Tumor Lung Metastasis Using OVA-immobilized γ-PGA Nanoparticle A. Materials B16-OVA cells which had been prepared by introducing OVA cDNA together with hygromycin B resistance gene into B16 melanoma cells were provided by Dr. Yasuharu NISHIMURA of Department of Immunogenetics, Faculty of Medical and Pharmaceutical Sciences, Kumamoto University. They were cultured using DMEM containing 10% FBS, 50 μM 2-ME and 200 μg/ml of hygromycin B. C57/BL6 mice ($H-2^b$; 7- to 10-week-old, female) were purchased from Japan SLC, Inc. Other materials are described above.

B. Methods

Figure 10:
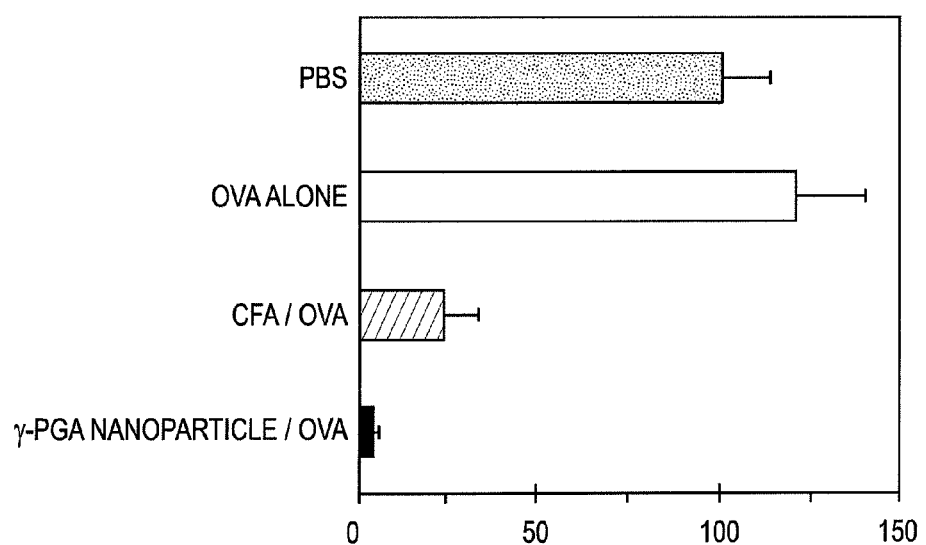
FIG. 10 represents results of tumor tests for suppressing lung metastasis suppression by OVA-immobilized γ-PGA nanoparticles.

B16-OVA cells ($1 \times 10^6$ cells) were administered into tail veins of C57BL/6 mice. On day 0, 3 and 7 after the inoculation, mice were immunized by administering subcutaneously to their backs OVA-incorporated γ-PGA nanoparticles (γ-PGA nanoparticle/OVA), OVA emulsified with CFA (CFA/OVA) or OVA solution (OVA alone) (n=9) prepared as described above. 100 μg of OVA was used. PBS was administered as a negative control. On day 25, lungs were removed and fixed with Bouin's solution (a saturated solution of picric acid: formaldehyde: glacial acetic acid=15:3:1). The number of the metastasized colonies on the surface of lung was counted under the stereoscopic microscope. The statistical significances were analyzed using Mann-Whitney test. The results are represented as percentage (%) to the number of the metastasized colonies in the group of the administration of PBS (FIG. 10).

C. Results

It was confirmed that the group of the immunization with γ-PGA nanoparticle/OVA (p<0.01) has effects of suppressing lung metastasis which prevent the lung engraftment of B16-OVA cells to lung which have high ability to metastasize to lung. Furthermore, the effects were stronger than those in CFA/OVA (p<0.01). It was confirmed that the γ-PGA nanoparticle/OVA is useful also for the treatment.

EXAMPLE 10

Evaluation of Safety of γ-PGA Nanoparticle by Histopathological Analysis of Site Administered with γ-PGA Nanoparticle A. Methods 10 mg/ml γ-PGA nanoparticle, CFA and IFA emulsified with equal volume of PBS, or PBS (20 μl/mouse) were administered subcutaneously to the footpads of mice. On day 7 after the administration, the footpads were amputated. They were fixed with 10% neutral buffered formalin and embedded into paraffin blocks. 5-μm tissue sections were prepared, and specimens were stained with hematoxylin-eosin to perform histopathological observation.

B. Results

In subcutaneous tissues of mice administered with CFA and IFA, inflammatory reactions were induced. In contrast, γ-PGA nanoparticles only slightly damaged the administered site, and little infiltration of inflammatory cells was observed (data not shown). It was confirmed that the γ-PGA nanoparticle has high safety.

INDUSTRIAL APPLICABILITY

The present invention provides a safe and effective adjuvant and a vaccine using the same. Therefore, the present invention can be used in the fields of medicine and the like (for example, the field of the preparation of the medicine for the prevention, treatment or diagnosis of diseases).

The invention claimed is:

1. A biodegradable nanoparticle, to which a virus antigen is immobilized, wherein the biodegradable nanoparticle has a poly(gamma-glutamic acid) coupled with L-phenylalanine ethyl ester as its backbone.

2. The biodegradable nanoparticle according to claim 1, wherein the viral antigen is selected from the group consisting of a retroviral antigen, an influenza viral antigen, a flaviviral antigen, a diarrhea viral antigen and a coronaviral antigen.

3. The biodegradable nanoparticle according to claim 2, wherein the viral antigen is a retroviral antigen.

4. The biodegradable nanoparticle according to claim 3, wherein the retroviral antigen is an HIV antigen.

5. The biodegradable nanoparticle according to claim 1, wherein the antigen is incorporated into the nanoparticle.

6. The biodegradable nanoparticle according to claim 1, wherein the antigen is present on the surface of the nanoparticle.

7. An immunogenic composition comprising the biodegradable nanoparticle according to claim 1.

8. The immunogenic composition according to claim 7, which is an anti-HIV immunogenic composition.

9. A method for the treatment of a disease in a subject, comprising administering the immunogenic composition according to claim 7 to the subject.

10. The method according to claim 9, wherein the disease is HIV.

11. A process for the manufacture of an immunogenic composition for the treatment of a disease, which comprises adding the biodegradable nanoparticle according to claim 1 to a pharmaccutically acceptable excipient or carrier.

12. The process according to claim 11, wherein the disease is HIV.

* * * * *